United States Patent [19]

Gassman

[11] 3,972,894

[45] Aug. 3, 1976

[54] SYNTHESIS OF OXINDOLES FROM ANILINES AND β-THIO CARBOXYLIC ESTERS OR AMIDES

[75] Inventor: Paul G. Gassman, Columbus, Ohio

[73] Assignee: The Ohio State University Research Foundation, Columbus, Ohio

[22] Filed: Feb. 27, 1975

[21] Appl. No.: 553,589

Related U.S. Application Data

[62] Division of Ser. No. 355,207, April 27, 1973, Pat. No. 3,897,451.

[52] U.S. Cl. .................. 260/325 R; 260/247.1 R; 260/293.73; 260/326.5 S; 260/470; 260/558 S

[51] Int. Cl.$^2$ .............. C07D 209/34; C07C 149/46; C07C 103/78; C07C 145/02

[58] Field of Search ............ 260/325 R, 470, 558 S

[56] References Cited

OTHER PUBLICATIONS

Gassman et al., "J.A.C.S.", vol. 95, pp. 2718–2719 (1973).

Primary Examiner—Lewis Gotts
Assistant Examiner—S. P. Williams
Attorney, Agent, or Firm—Gordon W. Hueschen

[57] ABSTRACT

Preparing oxindoles and intermediates therefor by reacting an N-haloaniline with β-thio esters or β-thio amides to form an azasulfonium halide, reacting the azasulfonium halide with a base to form an ortho-[thio-ether (hydrocarbonoxycarbonyl) alkyl]aniline, or a [thio-ether (aminocarbonyl) alkyl]aniline, reacting the orthosubstituted aniline with an acid to form a 3-thio-ether-2-oxindole, and then reducing the 3-thio-ether-2-oxindole with Raney Nickel to form the 2-oxindole.

11 Claims, No Drawings

SYNTHESIS OF OXINDOLES FROM ANILINES AND β-THIO CARBOXYLIC ESTERS OR AMIDES

The invention described herein was made in the course of work under a grant or award from the United States Department of Health, Education and Welfare.

This is a division of application Ser. No. 355,207, filed Apr. 27, 1973, now U.S. Pat. No. 3,897,451.

FIELD OF THE INVENTION

This invention relates to processes for making oxindoles and to intermediate compounds for use in such processes. More particularly, this invention provides an improved process –making oxindoles and some new intermediate compounds which can be used to prepare oxindoles.

Oxindoles have been used as intermediates in the preparation of various indole alkaloids. For detailed discussions of the presently-known methods of oxindole synthesis see *The Chemistry of Indoles*, by R. J. Sundberg, Academic Press, New York (1970).

The details of a stereospecific method for the orthoalkylation of aromatic amines was published in *Tetrahedron Letters*, 497 (1972). That procedure involved the addition of dialkylsulfides to the mono-N-chlorinated amine to give an azasulfonium salt, followed by ylid formation, and intramolecular attack of the ylid at the ortho position. In that way an aniline could be converted to a 2-alkylthioalkylaniline in good to excellent yield. Raney Nickel desulfurization then produced the 2-alkylaniline.

Other prior art that might be considered pertinent is the following: a) P. Claus and W. Vycudilik, *Monatsh. Chem.*, 101, 396 (1970), wherein Claus et al. reacted an aniline with a dimethylsulfoxide to form a sulfilimine, not an azasulfonium salt; and b) P. Claus, W. Vycudilik, and W. Rieder, *Monatsh. Chem.*, 102, 1571 (1971), wherein these sulfilimine compounds are thermally rearranged to hydrocarbon-S-hydrocarbon aromatic amine thio-ethers. Other papers which can be considered include a publication by Prof. C. R. Johnson et al., *Tetrahedron Letters*, No. 6, pp. 501–504 (1972), and "Indoles" Part I, by R. K. Brown, W. J. Houlihan, Ed., Wiley Interscience, New York (1972). In addition, the paper of U. Lerch and J. G. Moffatt entitled "Carbodiimide-Sulfoxide Reactions. XIII. Reactions of Amines and Hydrazine Derivatives" in the Journal of Organic Chemistry, Vol. 36, 3861 (1971) may be considered as pertinent as the Claus publications, supra.

However, none of that recent prior art discloses the hereindescribed method for preparing oxindoles. There is a need in the art for making oxindoles which are used as intermediates in making a wide variety of indole related products, many of which have significant physiological properties.

SUMMARY OF THE INVENTION

Briefly, it has been discovered that oxindoles can be prepared by reacting an N-haloaniline with a β-thio carboxylicester or amide under mild, substantially anhydrous conditions, in a solvent sufficiently polar to dissolve the reactants, to form an azasulfonium halide salt, and thereafter treating the azasulfonium salt with a base to form an ortho-[1-(thio-ether)-(hydrocarbonoxycarbonyl)alkyl]aniline or an ortho-[1-(thio-ether)-(aminocarbonyl)alkyl]aniline, which are believed to be new compounds, treating the ortho-substituted aniline with an acid to form a 3-thio-ether-2-oxindole compound. Thereafter, if desired, the 3-thio-ether-2-oxindole can be reduced, e.g., with Raney Nickel, to remove the thio-ether group and to form the 2-oxindole compound. This process can be conducted through its several steps up to the isolation of the 3-thio-ether-2-oxindole compound in one reaction vessel, without separation of the intermediate reaction products. However, the azasulfonium halide and the new ortho-substituted aniline compounds can be recovered and at least partially purified before continuing the process, if desired.

OBJECTS OF THE INVENTION

It is an object of the invention to provide an improved process for making 2-oxindoles using primary and secondary aromatic amines and β-thio carboxylic esters or β-thio-carboxylic amides as starting materials for the process.

It is another object of this invention to provide a process for making 2-oxindoles which enables a less tedious synthesis and the use of more readily available, less expensive, reactant chemicals under mild reaction conditions, and which process now permits the use of aniline starting materials containing substituents which otherwise could not be used.

It is also an object of this invention to provide some new ortho-substituted aniline compounds which find particular usefulness in a process for making 2-oxindoles therefrom.

Other objects, aspects, and advantages of the invention will become apparent to those skilled in the art from the specification and the claims which follow.

DETAILED DESCRIPTION OF THE INVENTION

According to the process of this invention, a primary or secondary aniline is first reacted with a source of positive halogen to prepare the N-haloaniline. Many sources of positive halogen are known and can be used to form the N-haloaniline. Examples of positive halogen sources for this reaction include tert.-butyl hypochlorite, N-chlorosuccinimide, calcium hypochlorite, sodium hypochlorite, sodium hypobromite, and the like. The N-chloroanilines are preferred for reasons of availability of reactants to make them and cost of materials, but other positive halogen compounds can be used to make useful N-haloanilines for use in this process.

The essential features of the process comprise:

a. reacting under substantially anhydrous conditions in an organic liquid diluent sufficiently polar to keep at least a portion of the reactants in solution at a temperature ranging from the Dry-Ice/Acetone mixture temperatures (about −78°C.) to about 10°C., preferably below 0°C., an N-haloaniline of the formula

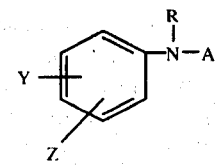

(I)

wherein

R is hydrogen, a hydrocarbon radical free from aliphatic unsaturation containing from 1 to 8 carbon atoms.

A denotes chlorine or bromine, but is preferably chlorine;

each of Y and Z is hydrogen or is a substituent which does not donate electrons more strongly than a methoxyl group in the meta position, and not more than one of Y and Z, as a substituent, is ortho to the —N(-R)A group position on the ring;

the —N(R)A group position having at least one ring carbon atom ortho thereto in an unsubstituted state;

with β-thio carboxylic ester or a β-thio carboxylic amide compound having a formula selected from the group consisting of

  (II)

and

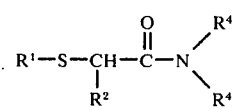  (III)

wherein

R¹ is lower alkyl, phenyl or benzyl;

R² is hydrogen, lower alkyl, phenyl or benzyl;

R³ is lower alkyl, phenyl or benzyl;

each R⁴ is hydrogen or lower alkyl, or the two R⁴ groups are taken together with the nitrogen to form a ring containing from 4 to 5 methylene carbon atoms and up to one ring oxygen atom, for a time sufficient to form an azasulfonium salt having a formula selected from the group consisting of

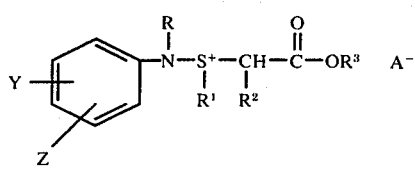  (IV)

and

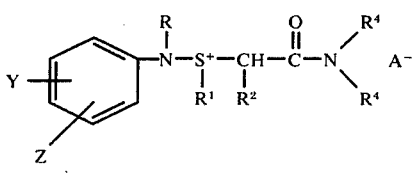  (V)

wherein Y, Z, R, R¹, R², R³, each R⁴ and A are as defined above;

b. reacting the azasulfonium salt of formula IV or V with a substantially anhydrous base, preferably one whose conjugate acid has a pKa greater than about 6, to effect rearrangement of the azasulfonium salt and to form an ortho-substituted aniline having a formula selected from the group consisting of

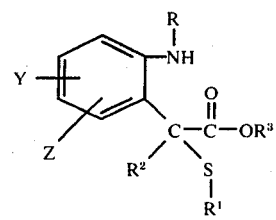  (VI)

and

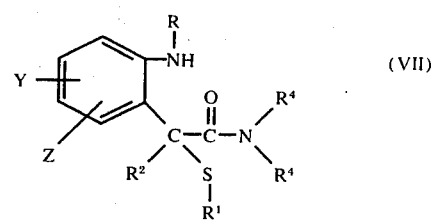  (VII)

wherein Y, Z, R, R¹, R², R³, and each R⁴ are as defined above;

c. either heating the ortho-substituted aniline compound of formula VI or VII to a temperature of from about 50°C. to about 150°C., or reacting the aniline with an acid, preferably an economical mineral acid such as aqueous hydrochloric acid, sulfuric acid, phosphoric acid or the like, to effect formation of a 3-thio-ether-2-oxindole compound of the formula

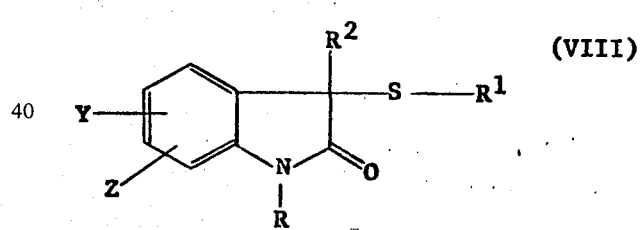  (VIII)

wherein Y, Z, R, R¹, and R² are as defined above; and, if desired, d. treating the 3-thio-ether-2-oxindole compound of the formula VIII with a desulfurizing reducing agent, e.g., with Raney Nickel, or its equivalent, to form a compound having the formula

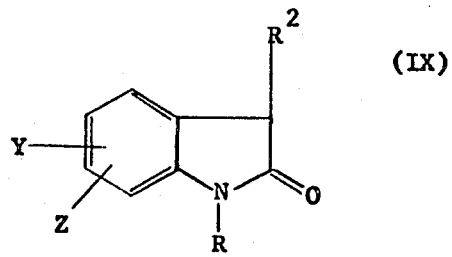  (IX)

wherein Y, Z, R, and R² are as defined above.

In the preferred embodiments for practicing the process, that is, the preferred choice of anilines for use in the process, are those wherein R is hydrogen or lower alkyl, A is chlorine, each of Y and Z is hydrogen or a halogen, nitro, cyano, lower alkyl, lower alkyloxy, lower acyloxy, a carbonyloxy-lower alkyl or a carbonyloxy-phenyl group. The preferred β-thio carboxylic ester compounds (II) for use in the process are those wherein R¹ is lower alkyl, R² is hydrogen or lower alkyl, R³ is lower alkyl. If the β-thio carboxylic amide compound (III) is used, the preferred ones are those wherein R¹ is lower alkyl, R² is hydrogen or lower alkyl, each R⁴ is hydrogen or lower alkyl.

The new compounds provided by this invention can be described as having a formula selected from the group consisting of

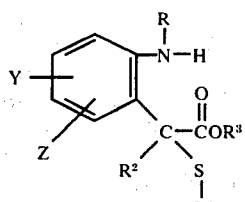

and

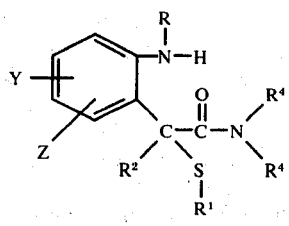

wherein R is hydrogen, a hydrocarbon radical free of aliphatic unsaturation and containing from 1 to 8 carbon atoms;

R¹ is lower alkyl, phenyl or benzyl;
R² is hydrogen, lower alkyl, phenyl or benzyl;
R³ is lower alkyl, phenyl or benzyl;
each R⁴ is hydrogen, lower alkyl, or the two R⁴ groups are taken together with the nitrogen to complete a ring containing 4 to 5 methylene carbon atoms and up to 1 ring oxygen atom;
each of Y and Z is hydrogen or a substituent selected from the group consisting of halogen, nitro, cyano, lower alkyl, lower alkyloxy, lower acyloxy, a carbonyloxy-lower alkyl and carbonyloxy-phenyl groups.

Preferred compounds of the above formulas (A) and (B) are those wherein R is hydrogen or lower alkyl, R¹ is lower alkyl, R² is hydrogen or lower alkyl, R³ is lower alkyl, and each R⁴ is hydrogen or lower alkyl.

Examples of the new compounds prepared according to the invention include:

2-[(methylthio)(methoxycarbonyl) methyl]aniline;
2-[1-(isopropylthio)-1-(ethoxycarbonyl)ethyl]-4-chloro aniline;
2-[1-(phenylthio)-1-(benzyloxycarbonyl)butyl]-3-nitroaniline;
2-[α-(ethylthio)-α-(butoxycarbonyl)benzyl]-3,4-dichloroaniline;
2-[(benzylthio)(phenoxycarbonyl)methyl]-4-cyanoaniline;
2-[(methylthio)(hexyloxycarbonyl)methyl]-4-methylaniline;
2-[1-(pentylthio)-1-(ethoxycarbonyl)-2-phenethyl]-3-methoxyaniline;
2-[(methylthio)(phenoxycarbonyl)methyl]-4-acetoxyaniline;
2-[1-(ethylthio)-1-(ethoxycarbonyl)ethyl]-3-ethoxycarbonylaniline;
2-[(methylthio)(propyloxycarbonyl)methyl]-3-bromoaniline;
2-[(ethylthio)(ethoxycarbonyl)methyl]-4-fluoroaniline;
2-[(methylthio)(N,N-dimethylaminocarbonyl)methyl]aniline;
2-[1-(methylthio)-1-(aminocarbonyl)ethyl]-3,4-dichloroaniline;
2-[(ethylthio)(N-ethylaminocarbonyl)methyl]-3-nitroaniline;
2-[1-(phenylthio)-1-(N,N-dibutylaminocarbonyl)ethyl]-4-methylaniline;
2-[(methylthio)(ethoxycarbonyl)methyl]-N-methylaniline;
2-[(ethylthio)(aminocarbonyl)methyl]-N-phenylaniline;
2-[1-(ethylthio)-1-(N,N-dimethylaminocarbonyl)propyl]-N-benzylaniline;
2-[α-(methylthio)-α-(piperidinocarbonyl)benzyl]-N-cyclohexylaniline;
2-[α-(phenylthio)-α-(1-morpholinocarbonyl)benzyl]-N-propylaniline;
2-[(benzylthio)(1-pyrrolidinocarbonyl)methyl]-N-ethylaniline, and the like.

As used herein, the term "lower alkyl" means a $C_1$ to $C_6$-alkyl radical, e.g., methyl, ethyl, propyl, isopropyl, n-butyl, isobutyl, tert.-butyl, n-pentyl, neopentyl, n-hexyl, and the like. The term "lower alkoxy" denotes a $C_1$ to $C_6$alkyl-O— group wherein the $C_1$ to $C_6$-alkyl is as exemplified above. The term "lower acyloxy" denotes formyloxy and a $C_1$ to $C_6$-alkyl-C(O)O— group wherein the $C_1$ to $C_6$-alkyl is as exemplified above. The term "lower alkanoyl" denotes formyl and a $C_1$ to $C_6$-alkyl-C(O)— group.

The aniline compounds which can be used as starting materials in this process are those which have a free, unsubstituted carbon position on the aromatic ring ortho to the amino nitrogen group. Such compounds are known or are obtainable by known procedures. Many of them are described in publications such as "Chem Sources", Directories Publishing Co., Flemington, N.J. 08822 (1972). The aniline may be unsubstituted or may contain one or more substituents, preferably not more than two substituents on aromatic ring carbon atoms. The substituents should be atoms or groups which do not donate electrons more strongly than a meta-, methoxy group. Not more than one of such substituents should be ortho to the —N(R)A group position. The —N(R)A group position of the aniline compound must have at least one ring carbon atom ortho thereto in the unsubstituted state. Examples of substituents which can be in the ring include halogen (fluorine, chlorine, bromine, iodine), nitro, cyano, lower alkyl, lower alkyloxy, lower acyloxy, a carbonyloxy-lower alkyl, and carbonyloxy-phenyl groups. Examples of useful starting compounds include aniline, chloroanilines such as 3-chloroaniline, 4-chloroaniline, 3,4-dichloroaniline, 3-fluoroaniline, 4-fluoroaniline, 3-bromoaniline, 4-bromoaniline, 4-iodoaniline, 3-nitroaniline, 4-nitroaniline, 3-cyanoaniline, 4-cyanoaniline, the toluidines such as 2-methylaniline, 3-methylaniline, 4-methylaniline, 4-ethylaniline, 4-hexylaniline, 3-propylaniline, 3-chloro-4-methylaniline, the lower alkyloxy-substituted anilines such as 3-methoxyaniline, 4-acetoxyaniline, 4-propionylaniline, 4-hexanoyloxyaniline, the 3- and 4- -carbonyloxy-lower alkylanilines such as benzocaine (4-ethoxy-carbonylaniline), 4-methoxycarbonylaniline, 3-propoxycarbonylaniline, as well as 3-phenoxycarbonylaniline, 4-phenoxycarbonylaniline, and the like. Secondary anilines which may be used include those having a $C_1$ to $C_8$-hydrocarbon group bonded to th amino nitrogen and include the $N$-$C_1$ to $C_8$-alkylanilines such as the N-methyl, N-ethyl, N-butyl, N-tert.-butyl, N-octylanilines as well as the N-phenyl, N-tolyl, N-xylylanilines and the N-cycloalkylanilines such as N-cyclopropyl, N-cyclobutyl, N-cyclopentyl, N-cyclohexyl, and N-cyclooctylanilines, and such compounds substituted on ring carbon atoms thereof with halogen, nitro, cyano, lower alkyl, lower alkyloxy, lower acyloxy, a carbonyloxy-lower alkyl or a carbonyloxy-phenyl as exemplified above.

The β-thio carboxylic esters and amide compounds of formulas II and III, above, are exemplified by the lower alkyl, phenyl and benzyl esters of α-loweralkylthio-, α-phenylthio and α-benzylthio lower alkanoic acids, phenylacetic acid, and phenylpropionic acids and the corresponding amides. Procedures for making such compounds are known in the literature, e.g., in an article by E. Bullmann and K. A. Jensen, *Bull. Chim. Soc.*, 5, 3, 2310 (1936), and in *Chem. Abstracts*, 52, p. 1265g (1958) by E. G. Howard. Examples of such starting materials include:
ethyl methylthioacetate
ethyl 2-methylthiopropionate
butyl 2-ethylthiobutyrate
phenyl 2-methylthio-2-phenylacetate
benzyl 2-benzylthiopropionate
methyl-2-phenylthioacetate
α-methylthioacetamide
α-ethylthiopropionamide
α-phenylthiobutyramide
α-benzylthioacetamide
2-propylthio-3-phenylpropionamide
α-methylthio-N,N-dimethylacetamide
α-ethylthio-N-methylpropionamide
α-methylthio-α-phenylacetamide
1-(α-methylthioacetyl)piperidine
1-(α-ethylthiopropionyl)morpholine
1-(α-methylthio-α-phenylacetyl)pyrrolidine, and the like.

The reactions of the process up to the point of base addition should be conducted in a liquid, substantially anhydrous medium which is sufficiently polar to dissolve at least a portion of the N-haloaniline and the β-thiocarboxylic ester or amide reactants at relatively low temperatures, e.g., from the cooled temperatures obtained by immersing the reaction vessel in a Dry Ice/Acetone mixture (about −78°C.) to about 10°C., preferably below about 0°C., up to the point of base addition, although the reaction temperature becomes less critical after the azasulfonium salt is formed. When the base addition is completed, the reaction mixture need not be cooled, and the temperature of the mixture can be allowed to rise to room temperature. The acid addition step can be conducted at any convenient temperature, for example, at 0°C. to 50°C.

The solvent used to dilute the reactants and to disperse the heat of reaction should be a compound or mixture of compounds which is liquid at reaction temperatures and which is sufficiently polar to solubilize at least a portion of the reactants. It can be, e.g., an alkyl halide such as methylene chloride, ethylenedichloride, chloroform, carbon tetrachloride, ethers such as diethyl ether, dipropyl ether, tetrahydrofuran, lower alkanols and alkylene glycols and glycol ethers such as methanol, ethanol, ethylene glycol, butyl ether of ethylene glycol, lower alkanonitriles such as acetonitrile, propionitrile, solvent mixtures containing the compounds of the above type, and the like.

The azasulfonium halide salt and base treatment steps of the process are conducted under substantially anhydrous conditions; that is, a reasonable degree of care is taken to avoid the introduction of water into the reaction mixture during these steps, although the introduction of small incidental amounts of water, introduced with solvents or reactants, is not substantially detrimental to the process.

The base which is reacted with the azasulfonium salt, IV or V, can be any base which will cause formation of an ylid intermediate, which will undergo a Sommelet-Hauser type of rearrangement, and effect hydrogen transfer to produce the ortho-substituted aniline of formula VI or VII. Bases which can be used for this purpose are those whose conjugate acids have a pKa of greater than about 6 and include, for examaple, alkanolic alkali metal hydroxides such as methanolic sodium hydroxide, potassium hydroxide, lithium hydroxide and calcium hydroxide, as well as sodium methoxide, potassium methoxide, sodium and potassium ethoxides, potassium and sodium carbonates, and organic bases such as lower alkyl amines such as ethylamine, diethylamine, triethylamine, tributylamine, and aromatic amines such as pyridine, the lutidines, and the like.

Treatment of the azasulfonium salt with the base results in rapid conversion of the azasulfonium salt through its unisolated intermediates to the derivative having formula VI if a β-thio carboxylic ester reactant had been used, or to the formation of intermediates having formula VII if the β-thio carboxylic amide had been used. The intermediate products VI and VII can be isolated, if desired, but this is not necessary. Both crude reaction mixtures containing compounds VI or VII can be treated with acid to form oxindole derivative of formula VIII.

As an example, a typical procedure could involve treating the selected aniline in methylene chloride solution at −65°C. with tert.-butyl hypochlorite, to form the N-chloroaniline, followed by the addition of the β-thio carboxylic ester or amide at −65°C., to form the azasulfonium salt and then with triethylamine to obtain the ortho-substituted aniline. These ortho-substituted anilines are thereafter treated with aqueous 2N hydrochloric acid to obtain the 3-methylthio-2-oxindole. These 3-thio-ether-2-oxindole products can be isolated and treated with Raney Nickel or equivalent reducing agents to remove the 3-thio-ether group and to form the 2-oxindole product of this process.

The new ortho-substituted aniline compounds having the chemical structures VI and VII above are useful as intermediates for preparing the corresponding 3-thio-ether-2-oxindole compounds having the chemical formula VIII, which in turn can be converted to 2-oxindole compounds having chemical formula IX above. Many of the 2-oxindoles which can be prepared by the new process of this invention are known useful compounds. The 2-oxindole products of the process of this invention can be used as intermediates in the preparation of indole alkaloids, as indicated above. In addition, the 2-oxindole compounds produced by the process of this invention can be used as intermediates in processes for preparing a wide variety of pharmaceutically useful compounds. For example, 2-oxindole compounds are used in the preparation of indole derivatives which are central nervous system depressants and anti-inflammatory drugs [Japanese Pat. No. 72–36,757 (1970); U.S. Pat. No. 3,686,210 (1972)]. Uses of 2-oxindoles in the synthesis of indole compounds are published by S. Sakai, *Yuki Gosei Kagaku Kyohai Shi*, 30, 434 (1972). In addition, 2-oxindoles of this invention can be used to make 2-oxindole compositions which are useful as anti-diarrheal agents (U.S. Pat. No. 3,585,866), anti-bacterials, anti-inflammatory agents (Japanese Pat. No. 71-14,898) [German Offen. No. 1,956,237 (1971)]; drugs useful in the treatment of arthritis [German Offen. No. 2,046,595 (1971)], and the like.

The invention is further exemplified by the following detailed examples and preparations which are given by way of illustration only. Temperatures recited herein are in degrees Centigrade unless otherwise indicated.

The following general procedure was used for the synthesis of 2-oxindoles from anilines and β-thio carboxylic esters and amides:

To a vigorously stirred solution of 0.044 mol of the aniline in 150 ml of methylene chloride at −65°C. was added dropwise a solution of 0.044 mol of t-butylhypochlorite in 20 ml of the same solvent to form the N-chloroaniline. After 5–10 minutes, 0.044 mol of the β-sulfide ester or amide dissolved in 20 ml of methylene chloride was added causing an exotherm, and stirring at −65°C. was continued for 1 hour to form the azasulfonium salt. Usually the azasulfonium salt did not precipitate. Subsequently, 0.044 mol of triethylamine in 20 ml of methylene chloride was added to form the ortho-substituted aniline. After the addition was completed the cooling bath was removed and the solution was allowed to warm to room temperature. A 50-ml portion of water was added and the organic layer was separated and evaporated. The residue was redissolved in 150 ml of ether and stirred overnight with 20 ml of 2N aqueous hydrogen chloride to form the 3-thioether-2-oxindole compound. In general, the 2-oxindole had precipitated and was collected by filtration. A second fraction could be obtained from the ether layer by concentrating it after it had been dried.

Desulfurization of the 3-methylthio-2-oxindoles was accomplished by stirring a solution of 0.5 to 2.0 g of the appropriate 3-methylthio-2-oxindole in 50 ml of absolute ethanol with an excess of Raney Nickel W-2 for 30 min. Filtration and evaporation gave a residue that was redissolved in methylene chloride and dried. After filtration the solvent was removed leaving pure desulfurized 2-oxindoles in yields generally varying from 70–85%.

W-2 Raney Nickel Preparation for Use

The W-2 Raney Nickel used in these experiments was obtained from W. R. Grace & Company, Raney Catalyst Division, South Pittsburg, Tennessee, as No. 28 Raney Active Nickel Catalyst in water. A portion of this was placed in a beaker and washed with distilled water until neutral to pH paper and then several more times with distilled water, three times with 95% ethanol, and three times with absolute ethanol. The catalyst under absolute ethanol was stored in brown bottles until use.

EXAMPLE 1

PREPARATION OF 5-METHYL-2-OXINDOLE AND INTERMEDIATES THEREFOR

Following the above procedure p-toluidine was converted to N-chloro-p-toluidine. The N-chloro-p-toluidine was treated with ethyl methylthioacetate to form the azasulfonium salt, of general formula IV above. The azasulfonium salt reaction mixture was then treated with triethylamine to obtain the ortho [(methylthio)(ethoxycarbonyl)methyl]-p-toluidine. Treatment of this ortho-substituted-p-toluidine with hydrochloric acid, as described, gave 2.88 g (0.015 mol, 34% yield) of 5-methyl-3-methylthioindole, m.p. 136°–137°:

This compound (recr. from methanol); ir (KBr) 3350 (NH) and 1680 cm$^{-1}$ (C=O): pmr (aceton-d$_6$) τ 0.78 (1H,s,NH), 2.80–3.30 (3H, m, aromatic H), 5.75 (1H, s, SCH), 7.72 and 7.94 (3H, s, CH$_3$ and SCH$_3$).

Anal. Calcd for C$_{10}$H$_{11}$NOS: C, 62.15; H, 5.74; N, 7.25; S, 16.59 Found: C, 61.85; H, 5.81; N, 7.14; S, 16.49.

Treatment of the 5-methyl-3-methylthio-2-oxindole with Raney Nickel, as described, gave the 5-methyl-2-oxindole in 55% yield, m.p. 171.5°–174° (Lit. m.p. 168°C.)

EXAMPLE 2

PREPARATION OF 4-NITRO-2-OXINDOLES AND INTERMEDIATES THEREFOR

Following the described procedure m-nitroaniline is converted to N-chloro-m-nitroaniline. The N-chloro-m-nitroaniline reaction mixture was treated with ethyl methylthioacetate to form the azasulfonium salt, having general formula IV. The azasulfonium reaction mixture is treated with triethylamine to form the ortho-[(methylthio)(ethoxycarbonyl) methyl]-m-nitroaniline. This ortho-substituted-m-nitroaniline intermediate is treated with hydrochloric acid to form 5.90 g (0.0268 mol., 61% yield) the 3-methylthio-4-nitro-2-oxindole, m.p. 228°–230°C.

(recr. from methanol); ir (KBr) 3350 (NH) and 1700 cm$^{-1}$ (C=O), pmr (DMSO-d$_6$) τ 0.30 (1H,s,NH), 2.28–2.82 (3H, m, aromatic H), 5.28 (1H, s, SCH), 8.08 (3H, s, SCH$_3$).

Anal. Calcd for C$_9$H$_8$N$_2$O$_3$S: C, 48.21; H, 3.60; N, 12.49; S, 14.30. Found: C, 48.27; H, 3.65; N, 12,38; S, 14.19.

EXAMPLE 3

PREPARATION OF 7-METHYL-2-OXINDOLES AND INTERMEDIATES THEREFOR

Ortho-toluidine was converted to the N-chloro-ortho-toluidine by the described procedure. This reaction mixture was treated with ethyl methylthioacetate to form the azasulfonium salt, having general formula IV. The azasulfonium salt was treated with triethylamine to form the 2-methyl-6-[(methylthio)(ethoxycarbonyl)methyl] aniline intermediate. This ortho-substituted aniline reaction mixture was treated with hydrochloric acid as described to obtain 5.65 g of the 7-methyl-3-methylthio-2-oxindole, (0.0294 mol., 67% yield), m.p. 194°–195°C.

(recr. from methanol); ir (KBr) 3350 (NH) and 1680 cm$^{-1}$ (C=O); pmr (DMSO-d$_6$) $\tau$ -0.42 (1H, s, NH), 2.80–3.30 (3H, m, aromatic H), 5.58 (1H, s, SCH), 7.82 and 8.02 (3H, s, CH$_3$ and SCH$_3$).

Anal. Calcd for C$_{10}$H$_{11}$NOS: C, 62.15; H, 5.74; N, 7.25; S, 16.59. Found: C, 61.90; H, 5.79; N, 7.17; S, 16.46.

Desulfurization of 1.0 g (5.2 mmol.) of the 7-methyl-3-methylthio-2-oxindole with Raney Nickel, as described above, gave a 72% yield of 7-methyl-2-oxindole, m.p. 206°–207°C., (Lit. 203°–204°C.).

EXAMPLE 4

PREPARATION OF 1-METHYL-2-OXINDOLE AND INTERMEDIATES THEREFOR

Following the above general procedure N-methylaniline was converted to the N-methyl-N-chloroaniline. The N-methyl-N-chloroaniline reaction mixture was treated with ethyl methylthioacetate to form the azasulfonium salt, having general formula IV. The azasulfonium salt reaction mixture was treated with triethylamine to form the 2-[(methylthio)(ethoxycarbonyl)methyl]-N-methylaniline. This ortho-substituted aniline was treated with hydrochloric acid to give 3.92 g (0.0203 mol., 46%, or 90% calculated on the unrecovered aniline) of 1-methyl-3-methylthio-2-oxindole, m.p. 87.5°–88.5°C. (recrystallized from ether).

ir (KBr) 1680 cm$^{-1}$ (C=O); pmr (CCl$_4$) $\tau$ 2.60–3.50 (4H, m, aromatic H), 5.98 (1H, s, SCH), 6.88 and 7.88 (3H, s, NCH$_3$ resp. SCH$_3$).

Anal. Calcd for C$_{10}$H$_{11}$NOS: C, 62.15; H, 5.74; N, 7.25; S, 16.59. Found: C, 62.09; H, 5.71; N, 7.43; S, 16.57.

Desulfurization of 0.50 g (2.59 mmol.) of the 1-methyl-3-methylthio-2-oxindole with Raney Nickel as described, gave a 77% yield of 1-methyl-2-oxindole, m.p. 83°–84.5°C. (Lit. m. p. 86°–88°C.).

EXAMPLE 5

PREPARATION OF 5-NITRO-2-OXINDOLE AND INTERMEDIATES THEREFOR

3-Methylthio-5-nitro-2-oxindole was obtained from p-nitroaniline and ethyl methylthioacetate by the general procedure using dichloromethane as a solvent. The nitroaniline (0.044 mol) was dissolved in 300 ml of dichloromethane. This solution was subsequently cooled under vigorous stirring to −70°C. resulting in a suspension to which the t-butylhypochlorite (0.044 mol), dissolved in 10 ml dichloromethane, was added. After a 3-hour period of stirring, most of the nitroaniline had dissolved and a solution of the sulfide (0.044 mol) in 10 ml of dichloromethane was added followed by an 8 hour period of stirring at −70°. From here on the procedure as described in the general procedure was followed giving 4.92 g (0.024 mol, 51%) of product, m.p. 196°–197° (recr. from methanol); ir (KBr) 3200 (N—H) and 1700 cm$^{-1}$ (c=O); pmr (DMSO-d$_6$) $\tau$ -1.53 (1H, s, NH), 2.00 and 3.15 (1H, dd, J=8, aryl H), 2.10 (1H, broad s, aryl H), 5.44 (1H, s, SCH) and 8.18 (3H, s, SCH$_3$).

Anal. Calcd for C$_9$H$_8$N$_2$O$_3$S: C, 48.21; H, 3.60; N, 12.49; S, 14.30. Found: C, 47.97; H, 3.75; N, 12.51; S, 14.17.

EXAMPLE 6

PREPARATION OF 3-METHYL-2-OXINDOLE AND INTERMEDIATES THEREFOR

Following the general procedure aniline was converted to N-chloroaniline. The N-chloroaniline reaction mixture was treated with ethyl 2-methylthiopropionate to form the azasulfonium chloride salt, having general formula IV. The azasulfonium chloride salt is treated with triethylamine to form the 2-[1-(methylthio)-1-(ethoxycarbonyl) ethyl] aniline. This ortho-substituted aniline was treated with hydrochloric acid to form 5.45 g (0.028 mol, 64% yield) of the 3-methyl-3-methylthio-2-oxindole, m.p. 150°–151° (recr. from benzene);

ir (KBr) 3200 (NH) and 1680 cm$^{-1}$ (C=O); pmr (CDCl$_3$) $\tau$ 0.40 (1H, s, NH), 2.50–3.20 (4H, m, aromatic H), 8.10 (3H, s, SCH$_3$) and 8.31 (3H, s, CH$_3$).

Anal. Calcd for C$_{10}$H$_{11}$NOS: C, 62.15; H, 5.74; N, 7.25; S, 16.59. Found: C, 62.11; H, 5.70; N, 7.30; S, 16.57.

Desulfurization of the 3-methyl-3-methylthio-2-oxindole (1.5 g, 7.75 mmol) gave a 70% yield of 3-methyl-2-oxindole, m.p. 122°–124° C. (Lit., 123°).

EXAMPLE 7

PREPARATION OF ETHYL α-(2-N-ACETAMINOPHENYL)-α-METHYLTHIOACETATE AND INTERMEDIATES THEREOF

Following the procedure described above aniline was converted to the N-chloroaniline, the N-chloroaniline was reacted with ethyl methylthioacetate to form the azasulfonium chloride salt, having general formula IV. The azasulfonium chloride salt was treated with triethylamine to form the 2-[(methylthio)(ethoxycarbonyl)-methyl] aniline.

Instead of purifying the residue by column chromatography, it was redissolved in 100 ml of dry ether and 20 ml of triethylamine. While stirring it at 0°, a solution of 3.4 g (0.044 mol) of freshly distilled acetyl chloride in 25 ml of dry ether was added to form the N-acetyl derivative. After 2 additional hours of stirring, 50 ml of water was added and the organic layer was dried over anhydrous magnesium sulfate, filtered and evaporated. The residue was subjected to column chromatography (silica gelmethylene chloride/ether) giving 7.07 g (0.0265 mol, 60%) of 21, m.p. 111°–114° (recr. from methanol); ir (KBr) 3220 (NH), 1700 and 1640 cm$^{-1}$ (C=O); pmr (CDCl$_3$) $\tau$ 1.27 (1H, s, NH), 2.00–3.00 (4H, m, aromatic H), 5.34 (1H, s, CHS), 5.82 (2H, q, OCH$_2$), 7.83 (3H, s, CH$_3$), 7.98 (3H, s, SCH$_3$) and 8.79 (3H, t, CH$_3$).

Anal. Calcd for C$_{13}$H$_{17}$NO$_3$S: C, 58.41; H, 6.41; N, 5.24; S, 11.99. Found: C, 58.24; H, 6.50; N, 5.23; S, 11.92.

This compound can also be named as N-acetyl-2-[(methyl-thio)(ethoxycarbonyl)methyl] aniline. It is useful for making 2-oxindoles by treatment with acid, as described above.

EXAMPLE 8

PREPARATION OF ETHYL α-(2-AMINOPHENYL)-α-METHYLTHIOACETATE, AND 2-OXINDOLE THEREFROM

Following the above-described procedure aniline was converted to N-chloroaniline. The N-chloroaniline was treated with ethyl methylthioacetate to form the azasulfonium salt and the azasulfonium salt was treated with triethylamaine to form 6.12 g (0.027 mol, 62% yield) of the ethyl α-(2-aminophenyl)-α-methylthioacetate, as a yellow oil. It can also be named 2-[(methylthio)(ethoxycarbonyl)methyl] aniline. It had the following analyses:

(undistilled) ir 3350 ($NH_2$) and 1700 $cm^{-1}$ (C=O); pmr ($CCl_4$) τ 2.80–3.55 (5H, m, aromatic H), 5.48 (1H, s CHS), 5.85 (2H, q, $OCH_2$), 6.02 (2H, s, $NH_2$), 8.05 (3H, s, $SCH_3$), 8.80 (3H, t, $CH_3$).

The compound is useful as an intermediate in preparing 2-oxindoles by treatment with acid as described below.

Cyclization of ethyl α-(2-aminophenyl)-α-methylthioacetate to 3-methylthio-2-oxindole was accomplished by stirring 2.00 g (8.9 mmol) of that acetate in 20 ml of ether for 4 hours with 10 ml of 2N hydrochloric acid. The ethereal layer was dried over anhydrous sodium sulfate, filtered and evaporated, giving 1.34 g. (7.5 mmol, 84%) of 3-methylthio-2-oxindole, m.p. 126°–127° (recr. from ether); ir (KBr) 1700 (C=O) and 3350 $cm^{-1}$ (NH); pmr ($CCl_4$) τ - 0.08 (1H, s, NH), 2.70–3.20 (4H, m, aromatic H), 5.88 (1H, s, SCH), 7.84 (3H, s, $SCH_3$).

Anal. Calcd for $C_9H_9NOS$: C, 60.31; H, 5.06; N, 7.82; S, 17.89. Found: C, 60.16; H, 5.19; N, 7.71; S, 17.70.

Desulfurization of the 3-methylthio-2-oxindole (2.0 g, 0.011 mol) gave in 76% 2-oxindole as confirmed by comparison with an authentic sample.

EXAMPLE 9

PREPARATION OF 3-METHYLTHIO-2-OXINDOLE DIRECTLY FROM ANILINE AND ETHYL METHYLTHIOACETATE WITHOUT ISOLATION OF ETHYL α-(2-AMINOPHENYL)-α-METHYLTHIO-ACETATE

Following the procedure described above, aniline is converted to N-chloroaniline. The N-chloroaniline is treated with ethyl methylthioacetate to form the azasulfonium salt. The azasulfonium salt reaction mixture is treated with triethylamine to form the ethyl α-(2-aminophenyl)-α-methylthio-acetate, and this orthosubstituted aniline reaction mixture is treated with hydrochloric acid to obtain 4.95 g (0.0276mol, 63% yield) of 3-methylthio-2-oxindole. This 3-methylthio-2-oxindole can be reduced to 2-oxindole with Raney Nickel by procedures described above.

EXAMPLE 10

PREPARATION OF 2-OXINDOLE FROM ANILINE AND METHYLTHIO ACETAMIDE

A. To a suitable reaction vessel containing 8.0 g (0.088 mol) of aniline in 250 ml of tetrahydrofuran (THF) at −70° there was added a solution of 9.2 g (0.088 mol) of tert-butylhypochlorite in 15 ml of THF to form the N-chloroaniline. After 10 minutes a solution of 9.3 g (0.088 mol) of methylthioacetamide in 200 ml of THF was added quickly to prevent crystallization of the amide while maintaining the temperature below −40° to form the acetamidoanilino-methyl sulfonium chloride (V).

Almost instantaneously a precipitate was formed. Stirring was continued for 2 hours and after warming to room temperature the precipitate was collected by filtration. Drying resulted in 18.10 g (0.078 mol, 89%) of the sulfonium chloride: dec. 107°–108°; ir (KBr) 1670 (C=O) $cm^{-1}$; pmr (DMSO-$d_6$) τ -0.57 (1H, s, NH), 1.70 and 2.20 (1H, s, $NH_2$), 2.30–3.10 (5H, m, aryl H), 5.00 and and 5.20 (1H, d, J=16 Hz, $^+SCH_2$) and 6.60 (3H, s, $^+SCH_3$).

An analytical sample was obtained by dissolving 0.5 g of the salt in 3 ml of dimethyl sulfoxide and pouring it into 20 ml of THF. The solid was filtered and washed with THF.

Anal. Calcd for $C_9H_{13}ClNOS$: C, 46.45; H, 5.63; N, 12.04; S, 13.78; Cl, 15.23. Found: C, 46.15; H, 5.65; N, 11.95; S, 13.86; Cl, 15.44.

B. To a stirred suspension of 4.0 g (0.0172 mol) of above sulfonium chloride in 100 ml of methylene chloride there was added 2.3 g (0.021 mol) of triethylamine and the mixture was stirred for 1 hour to form the α-(2-aminophenyl)-α-(methylthio)acetamide. This compound can also be named as 2-[(methylthio)-(aminocarbonyl)methyl] aniline. To the clear solution there was added 25 ml of water, and after separation of layers, the organic layer was dried over anhydrous magnesium sulfate, filtered and evaporated to leave 2.83 g (0.0145 mol, 84% yield) of α-(2-aminophenyl)-α-methylthio)acetamide as a solid residue, m.p. 98.5°–99.5° C (recr. from chloroform);

ir 3250 ($NH_2$) and 1650 $cm^{-1}$ (C=O); pmr ($CDCl_3$) 2.70–3.90 (6H, m, NH2 and aryl H), 5.39 (1H, s, CHS), 5.66 (2H, s, $NH_2$), 7.88 (3H, s, $SCH_3$).

Anal. Calcd for $C_9H_{12}N_2OS$: C, 55.08; H, 6.16; N, 14.27; S, 16.33. Found: C, 54.79; H, 6.19; N, 14.19; S, 16.30.

C. To a 1.70 g portion (0.0087 mol) of the α-(2-aminophenyl)-α-(methylthio)acetamide in 60 ml of ethanol, stirred for 24 hours, there was added 1 ml of concentrated hydrochloric acid to effect ring closure of the ortho-substituted aniline and to form 3-methylthio-2-oxindole. The resulting solution was concentrated to about 15 ml and poured into 75 ml of water. The precipitate was collected by filtration and after drying there was obtained 1.22 g (0.0068 mol, 78% yield) of 3-methylthio-2-oxindole, m.p. 125°–127°.

D. The 3-methylthio-2-oxindole can be converted to 2-oxindole by treatment with Raney Nickel as described above.

EXAMPLE 11

PREPARATION OF 5-CARBOETHOXY-7-METHYL-2-OXINDOLE AND INTERMEDIATES THEREFOR

By the procedure described above, 4-ethoxycarbonyl-2-methylaniline was converted to the N-chloro-4-carboethoxy-2-methylaniline on a 0.015 mol scale. The N-chloroaniline was treated with ethyl methylthioacetate to form the azasulfonium chloride salt, having general formula IV. The azasulfonium chloride salt was treated with triethylamine to form the 2-methyl-4-carboethoxy-6-[(methylthio)(ethoxycarbonyl)methyl] aniline. The resulting substituted aniline was treated with hydrochloric acid to form 2.45 g (66% yield) of 5-ethoxycarbonyl-7-methyl-3-methylthio-2-oxindole, m.p. 195°–196° C. (recr. from methanol);

ir (KBr) 3350 (NH), 1700 and 1680 cm$^{-1}$ (C=O); pmr (CDCl$_3$) τ 0.12 (1H, s, NH), 2.08 (2H, m, arylH), 5.58 (2H, q, OCH$_2$), 5.65 (1H, s, CHS), 7.62 and 7.90 (3H, s, CH$_3$ and SCH$_3$), 8.59 (3H, t, CH$_3$).

Anal. Calcd for C$_{13}$H$_{15}$NO$_3$S: C, 58.85; H, 5.70; N, 5.28; S, 12.08. Found: C, 58.84; H, 5.77; N, 5.17; S, 11.93.

An 0.80 g (3.01 mmol) portion of the 5-ethoxycarbonyl-7-methyl-3-methylthio-2-oxindole in 130 ml of absolute ethanol was treated with Raney Nickel by the above described procedure to give 0.44 g (2.01 mmol, 67% yield) of 5-ethoxycarbonyl-7-methyl-2-oxindole, m.p. 238°–241°;

ir (KBr) 1700 and 1670 cm$^{-1}$ (C=O); pmr (DMSO-d$_6$)-0.50 (1H, s, NH), 2.54 (2H, s, arylH), 5.83 (2H, q, J=6.0 Hz, (OCH$_2$), 6.52 (2H, s, CH$_2$), 7.80 (3H, s, CH$_3$), 8.71 (3H, t, J=6.0 Hz, OCH$_2$CH$_3$).

Anal. Calcd for C$_{12}$H$_{13}$NO$_3$: C, 65.74; H, 5.98; N, 6.39. Found: C, 65.71; H, 5.94; N, 6.43.

Additional compounds which can be prepared by the procedure described above include:

5-chloro-2-oxindole from N,4-dichloroaniline and ethyl methylthioacetate, 4,5-dibromo-2-oxindole from N,3,4-tribromoaniline and ethyl methylthioacetate, 5-cyano-2-oxindole from N-chloro-4-cyanoaniline and methyl methylthioacetate, 5-isopropyl-2-oxindole from N-chloro-4-isopropylaniline and α-methylthioacetamide, 5-ethoxy-3-methyl-2-oxindole from N-chloro-4-ethoxyaniline and α-ethylthiopropionamide, 5-propionoxy-2-oxindole from N-chloro-4-propionoxyaniline and α-benzylthioacetamide, 5-propyloxycarbonyl-3-methyl-2-oxindole from N-chloro-4-propyloxycarbonylaniline and ethyl 2-methylthiopropionate, 5-phenoxycarbonyl-3-phenyl-2-oxindole from N-chloro-4-phenoxycarbonylaniline and α-methylthio-α-phenylacetamide, 3-benzyl-2-oxindole from N-chloroaniline and 2-methylthio-3-phenyl-propionamide, and the like.

I claim:

1. A process which comprises reacting in an organic liquid solvent which is sufficiently polar to dissolve at least a portion of the reactants under substantially anhydrous conditions at a temperature of from about −78°C. to about 10°C. a compound of the formula:

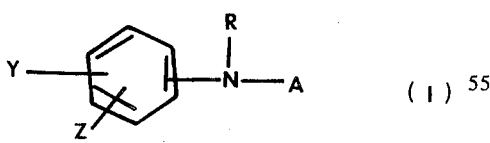

wherein
R is hydrogen or a hydrocarbon radical free of aliphatic unsaturation containing from 1 to 8 carbon atoms;
A is chlorine or bromine;
each of Y and Z is hydrogen or a substituent which does not donate electrons any more strongly than a meta methoxy group, and not more than one of Y and Z, as a substituent, is ortho to the —N(R)A group position on the ring; the —N(R)A group position having at least one ring carbon atom ortho thereto in an unsubstituted state;

with a β-thio carboxylic ester or amide having a formula selected from the group consisting of

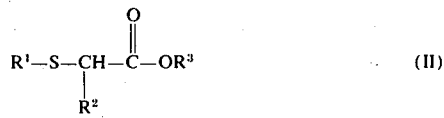

and

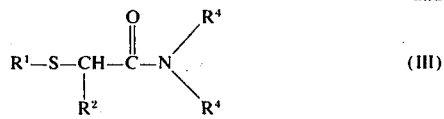

wherein
R$^1$ is lower alkyl, phenyl or benzyl;
R$^2$ is hydrogen, lower alkyl, phenyl or benzyl;
R$^3$ is lower alkyl, phenyl or benzyl;
each R$^4$ is hydrogen, lower alkyl, or the two R$^4$ groups are taken with the nitrogen to complete a ring containing from 4 to 5 methylene carbon atoms and up to one ring oxygen atom; for a time sufficient to form an azasulfonium salt having a formula selected from the group consisting of

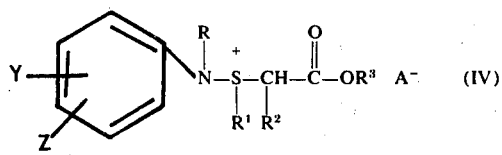

and

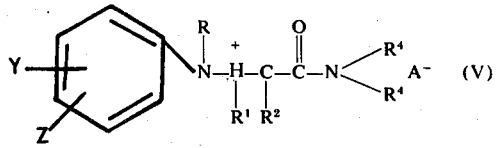

wherein Y, Z, R, R$^1$, R$^2$, R$^3$, each R$^4$ and A are as defined above, and at least one of the phenyl ring carbon atoms ortho to the nitrogen is in the unsubstituted state.

2. A process as defined in claim 1 in which an azasulfonium salt of formula IV or V is reacted with a substantially anhydrous base to effect rearrangement of the azasulfonium salt and to form an amino compound having a formula selected from the group consisting of

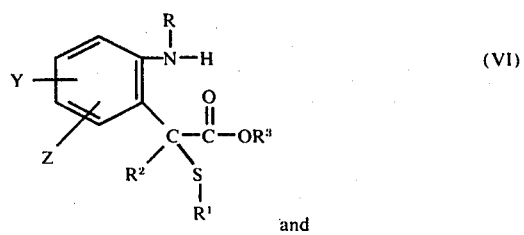

and

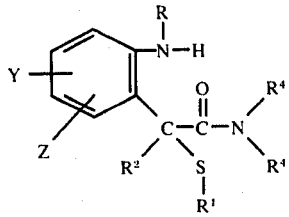

(VII)

wherein Y, Z, R, R¹, R², R³, and R⁴ are defined in claim 1.

3. A process as defined in claim 2 wherein an amino compound of formula VI and VII is treated with an acid or heated to from about 50°C. to about 150°C. to form an oxindole compound of the formula

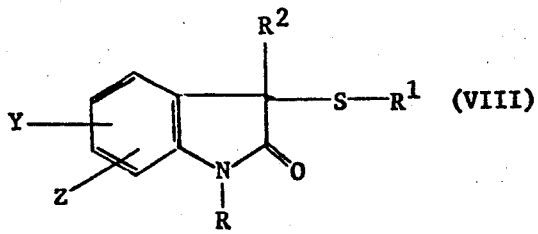

(VIII)

wherein Y, Z, R, R¹ and R² are as defined in claim 1.

4. A process as defined in claim 3 wherein the oxindole compound of formula VIII is treated with a de-sulfurizing reducing agent to form a compound of the formula

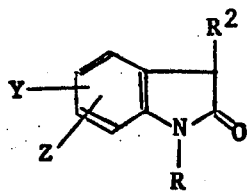

(IX)

wherein Y, Z, R, and R² are as defined in claim 1.

5. A process as defined in claim 4 wherein R is hydrogen, A is chlorine; each of Y and Z is selected from the group consisting of hydrogen and halogen, nitro, cyano, lower alkyl, lower alkyloxy, lower acyloxy, carbonyloxy-lower alkyl and carbonyloxy-phenyl groups;

the sulfur containing compound has formula II wherein R¹ is lower alkyl, R² is hydrogen and R³ is lower alkyl to form a compound of the formula

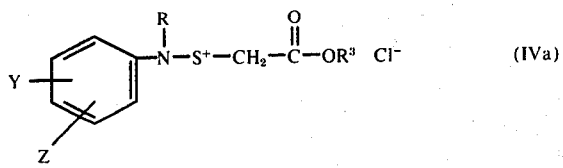

(IVa)

wherein Y, Z, R and R³ are as defined herein.

6. A process as defined in claim 5 wherein an N-chloro-4-carboethoxyaniline is reacted with ethyl methylthioacetate to form the azasulfonium chloride, the resulting azasulfonium chloride is reacted with a tris (lower alkyl) amine, to form 2-[(methylthio)(ethoxycarbonyl)methyl]-4-carboethoxyaniline, and the aniline is treated with an acid to form the 3-methylthio-5-carboethoxy-2-oxindole.

7. A process as defined in claim 6 which further includes the step of treating the 3-methylthio-5-carboethoxy-2-oxindole with a desulfurizing reducing agent to form 5-carboethoxy-2-oxindole.

8. A process as defined in claim 7 wherein the reducing agent is Raney Nickel.

9. A process as defined in claim 5 wherein an N-chloro-toluidine is reacted with ethyl methylthioacetate to form the azasulfonium chloride, the azasulfonium chloride is treated with a tris (lower alkyl) amine to form a 2-[(methylthio)(ethoxycarbonyl)methyl] toluidine, and the resulting toluidine is treated with an acid to form a 3-methylthio-2-oxindole of the formula

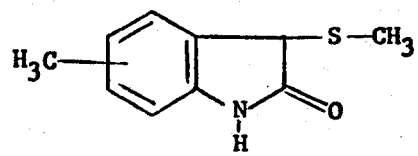

10. A process as defined in claim 9 wherein the 3-methylthio-2-oxindole is treated with a de-sulfurizing reducing agent to form an oxindole of the formula

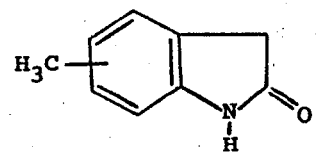

11. A process as defined in claim 10 wherein the de-sulfurizing reducing agent is Raney Nickel.

* * * * *

UNITED STATES PATENT OFFICE
CERTIFICATE OF CORRECTION

Patent No. 3,972,894          Dated August 3, 1976

Inventor(s) PAUL G. GASSMAN

It is certified that error appears in the above-identified patent and that said Letters Patent are hereby corrected as shown below:

Column 16, line 40

Reads:                        Should Read:

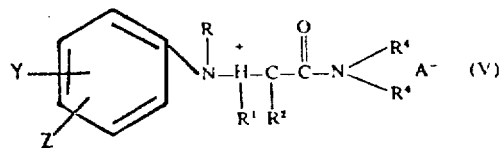   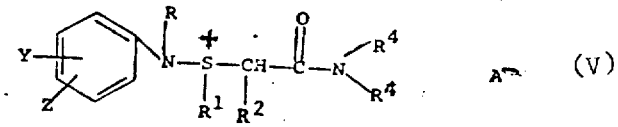

Signed and Sealed this

Nineteenth Day of October 1976

[SEAL]

Attest:

RUTH C. MASON
*Attesting Officer*

C. MARSHALL DANN
*Commissioner of Patents and Trademarks*

UNITED STATES PATENT OFFICE
CERTIFICATE OF CORRECTION

Patent No. 3,972,894          Dated August 3, 1976

Inventor(s) Paul G. Gassman

It is certified that error appears in the above-identified patent and that said Letters Patent are hereby corrected as shown below:

Column 18, lines 5 through 14: --

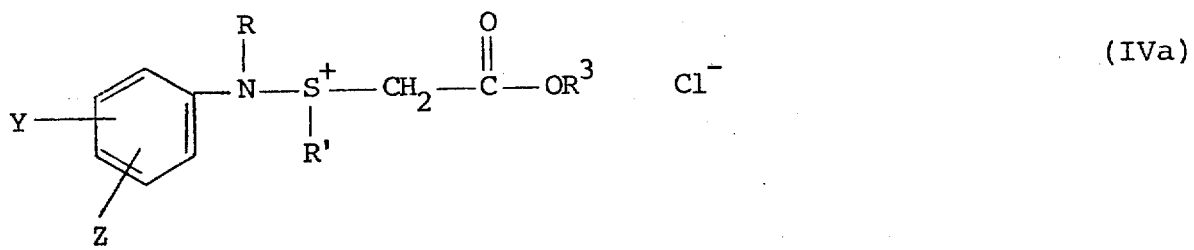

wherein Y, Z, R, R' and $R^3$ are as defined herein. --.

Column 7, line 20: Change "th" to -- the --.

Signed and Sealed this

Eighth Day of February 1977

[SEAL]

Attest:

RUTH C. MASON
Attesting Officer

C. MARSHALL DANN
Commissioner of Patents and Trademarks